United States Patent [19]

Stevenson et al.

[11] Patent Number: 5,495,058
[45] Date of Patent: Feb. 27, 1996

[54] NON-OZONE DEPLETING CHLORINATION SOLVENTS

[75] Inventors: Donald R. Stevenson; Satyanarayana Kodali, both of Dover, Ohio

[73] Assignee: Dover Chemical Corporation, Dover, Ohio

[21] Appl. No.: 248,758

[22] Filed: May 25, 1994

[51] Int. Cl.$^6$ .................................................. C07C 17/10
[52] U.S. Cl. ................................................................ 570/252
[58] Field of Search ................................................ 570/252

[56] References Cited

U.S. PATENT DOCUMENTS

| | | | |
|---|---|---|---|
| 2,941,013 | 6/1960 | Jenney | 570/252 |
| 3,431,314 | 3/1969 | Olinger et al. . | |
| 3,567,610 | 3/1971 | Krol et al. . | |
| 3,577,472 | 5/1971 | Jubin et al. . | |
| 3,584,066 | 6/1971 | Reni . | |
| 3,654,107 | 4/1972 | Lindwall et al. . | |
| 3,848,006 | 11/1974 | Sparks . | |
| 3,896,183 | 7/1975 | Henderson et al. . | |
| 3,948,741 | 4/1976 | McCoy . | |
| 4,052,471 | 10/1977 | Pearsall . | |
| 4,100,212 | 7/1978 | DiFiore et al. . | |
| 4,329,525 | 5/1982 | Riegel et al. . | |
| 4,614,572 | 9/1986 | Holbrook et al. . | |

*Primary Examiner*—Alan Siegel
*Attorney, Agent, or Firm*—Oldham & Oldham, Co.

[57] ABSTRACT

A process for the chlorination of a paraffin wax is described which includes the steps of contacting the paraffin wax or partially chlorinated paraffin wax with chlorine wherein the improvement is the use of a non-ozone depleting aromatic solvent with a boiling point less than 180° C., preferably less than 160° C. and which is non-reactive to chlorine in a free radical chlorination environment, in contrast to typical $C_1$–$C_2$ aliphatic solvents.

11 Claims, No Drawings

NON-OZONE DEPLETING CHLORINATION SOLVENTS

TECHNICAL FIELD

The invention described herein pertains generally to the use of non-ozone depleting solvents in the manufacture highly chlorinated resins.

BACKGROUND OF THE INVENTION

Chlorinated paraffins are classified as chlorinated hydrocarbons that have the general formula $C_xH_{(2x-y+2)}Cl_y$. They were first prepared in 1858 by P. A. Bollcy. Significant commercial uses did not develop until the early 1930's when they were first used for fire-retardant and water-proof canvas material, and in the metal working industry as extreme pressure additives for lubricating oils. The raw materials used in the chlorination reaction consist of petroleum fractions such as normal paraffins, at least 90% linear, and wax fractions averaging as many as 30 carbon atoms. While there are a number of raw materials available, those used for the production of chlorinated paraffins fall into three categories: (1) a $C_{12}$ fraction that normally includes $C_9$–$C_4$ hydrocarbons; (2) a $C_{15}$ fraction that normally includes $C_{13}$–$C_{17}$ hydrocarbons; and (3) a $C_{24}$ fraction that normally includes $C_{20}$–$C_{30}$ hydrocarbons. The selection of a particular raw material is dependent on the desired properties of the final chlorinated paraffin. Isoparaffins (usually<1%), aromatics (usually<100 ppm), and metal contamination are kept as low as economically feasible since their presence results in products with undesirable properties.

In the United States, approximately 50% of the chlorinated paraffins, are used as extreme pressure lubricant additives in the metal working industry. About 25% are used in plastics, including fire retardant and water repellent coated fabrics. The remainder are used in rubber, caulks, and sealants.

Commercial chlorinated paraffins have a range of between ~20–75% chlorine content. The bulk of the manufactured products fall within the 40–70% chlorine range. Chlorine content as used herein, refers to the amount of chlorine chemically fixed or bonded to the paraffin and not to any free chlorine or the chlorine content of any residual chlorinated solvent remaining in the chlorinated hydrocarbon material. The important physical properties of the chlorinated paraffins include viscosity, solubility, color, and thermal instability. For a given paraffin, increasing chlorine content increases viscosity and specific gravity. With chlorinated paraffins of the same chlorine content, lower viscosities are observed for the lower molecular weight paraffins.

The techniques for chlorinating $C_{20-30}$ paraffins has long been known. When a product exhibiting a relatively low degree of chlorination is desired, e.g., up to about 40% chlorine by weight, the use of a solvent may generally be avoided. By the elimination of a solvent from the system, the effective capacity of the reaction vessel is increased and product recovery techniques are simplified. When higher chlorine contents, eg. about 55–73% by weight, the $C_{20-30}$ paraffin hydrocarbon wax, is typically dissolved in an organic solvent which is inert, in the sense that it does not interfere with the desired reaction and which also serves as a diluent during the chlorination reaction. Since the chlorination reaction is exothermic, the intimate presence of the solvent is helpful in maintaining the desired reaction temperature. A solvent may be selected having the requisite boiling point so that heat from the reaction zone may be withdrawn as the solvent is refluxed. While the use of a solvent has been described, paraffins of $C_{10-13}$ and $C_{13-17}$ do not require a solvent, even up to 65–70% chlorine levels. However, the C18–30 product obtained by neat chlorination is a dark colored product with poor stability when chlorine contents of over 65% are attempted.

Preferred solvents are halogenated $C_1$ or $C_2$ hydrocarbons. For instance, carbon tetrachloride, chloroform, pentachloroethane, perchloroethylene, 1,1,1-trichloroethane, 1,1,2-trichloroethane, and ethylene dichloride may serve this role. U.S. Pat. No. 3,948,741 teaches that a diluent-solvent should possess enough chlorine or fluorine moleties to render it substantially inert, i.e., toward further chlorination at the conditions of the reaction. The preferred diluent-solvent was indicated to include hydrocarbons wherein at least about 30% of the hydrogen atoms were replaced by chlorine or fluorine. Among the preferred diluent-solvents were perfluorinated or perchlorinated (or perfluoro-perchloro) alkanes including normal and branched-chain alkanes.

The '741 patent indicated that the diluent-solvent could include inert substituents. Certain substituents, which were inert as above defined, were indicated to in fact, increase the selectivity of the reaction, i.e., the synthesis of 1-chloro normal alkanes. Examples of such insert substituents included hydroxy, nitrile, carboxylic acid, carboxylic acid ester, and ketone functionalities. It was additionally taught that aromatic rings, sulfides, nitro groups, amines and phosphines when present as substituents in the diluent solvent (used alone) caused a decrease in the desired selectivity, and therefore it was preferred not to use diluent-solvents alone which contained these moieties. The particularly preferred solvent is carbon tetrachloride. Analogous chlorofluoroalkanes, hexachlorobutadiene, and many other solvents suitably inert under the reaction conditions may also be used as will be apparent to those skilled in the art. Additional examples of such would include: trifluoroacetic acid, trichloroacetic acid, 2,2,2-trichloroethanol, trichlorofluoromethane, hexachloroacetone, trichloroacetonitrile, pentachloroethylene, ethyl heptafluorobutyrate, ethyl trifluoroacetate, methylene dichloride, 1,2-dichloroethane, 1,1,2-trichloro- 1,2,2-trifluoroethane, 1,2,3,4-tetrachlorobutane, octachloropropane, heptachloroisobutanes (mixed isomers), 1,1-dichloro-1,1,2,2-tetrafluoroethane, and hexachloroethane.

Chlorinated paraffins are typically produced by passing chlorine gas into a liquid paraffin directly, with or without a solvent, or into a solubilized paraffin solution. The chlorination reaction is a typical substitution reaction and hydrogen chloride is formed as a by-product. Because of the corrosive nature of the hydrogen chloride reaction by-product and chlorine gas reactant, special care must be given to materials of construction. Ultraviolet light is often used to promote chlorination, especially at higher chlorine contents.

Chlorine feed rates and reaction temperatures differ slightly among the different producers. The reaction is exothermic and temperatures are usually kept at 50°–100° C. The following techniques may be employed to moderate the exothermic portion of the reaction and to maintain the desired temperature: (1) refluxing the solvent with the concomitant removal of heat from the reaction mixture; (2) cooling the walls of the reactor; and (3) controlling the rate of chlorine introduction. The exact temperature selected for optimum results will be influenced by (1) the boiling range of the solvent; (2) the reaction pressure on the vessel used during the chlorination; and (3) the relative concentration of paraffin in the solvent. Manufacture of resinous chlorinated paraffins (70% chlorine content), generally requires the use of a solvent, such as carbon tetrachloride to dissolve the intermediate chlorinated paraffin and to allow the chlorine level to increase to the 70% level where the product is a definite solid with sufficient hardness to be ground and processed as a powder after solvent stripping. However, it is possible to prepare a 70% chlorinated resin without a solvent. But this procedure requires higher temperatures, e.g., 135° C., and takes a long time due to high viscosity. The final product is typically darkly colored, with poor stability.

Carbon tetrachloride however, is undesirable because it is believed to cause cancer and has been implicated in potential ozone layer depletion. Virtually all homologous solvents that could be used as a substitute for carbon tetrachloride have similar problems. If they are significantly higher in molecular weight, their higher boiling point makes it difficult to remove the solvent from the chlorinated wax product.

Thus, in general, highly chlorinated resins are generally prepared by starting with a $C_{20}$–$C_{24}$ essentially linear material, which under modest pressure (e.g. 5–10 psig), if any pressure is used at all, is chlorinated using neat chlorine, producing a highly viscous oil, of roughly 50% chlorinated 5paraffin. This material is now soluble in, for example, $CCl_4$, in which a roughly 50/50 mixture of chlorinated solvent and partially chlorinated paraffin is refluxed and chlorine is introduced. This exothermic reaction is limited in rate to the cooling capacity of the production equipment. HCl is a by-product of the reaction. The mixture is reacted with chlorine until approximately 70% chlorine containing chlorinated paraffin resin is produced. The bulk of the solvent $CCl_4$ is distilled off. Residual $CCl_4$ is however, quite difficult to remove. In one method, $CCl_4$ is removed by melting the chlorinated paraffin resin at about 140° C., thereby reducing the level of residual $CCl_4$ to ~1–2%. This amount can be further reduced to about less than 0.1% by using vacuum stripping. Upon chilling the chlorinated paraffin resin, the product can be reduced in particle size by using a hammer mill.

However to date, there still exists the need to provide a chlorination process which can be used to manufacture highly chlorinated resins without using ozone-depleting organic solvents, especially chlorinated solvents which are difficult to remove from the product in finished form.

SUMMARY OF THE INVENTION

In accordance with the present invention, there is provided a chlorination process for obtaining chlorinated resins without using ozone-depleting organic solvents, especially chlorinated alkane-based solvents which are difficult to remove from the final product.

It is an object of this invention to provide a non-ozone depleting halogenated aromatic solvent useful for the chlorination of paraffin resins.

It is a further object of this invention to provide a non-ozone depleting perhalogenated aromatic solvent useful for the chlorination of paraffin resins.

These and other objects of this invention will be evident when viewed in light of the derailed description and appended claims.

DETAILED DESCRIPTION OF THE INVENTION

The chlorination process of this invention is based on the use of chlorinated aromatic solvents or fluorinated aromatic solvents or chlorinated and/or fluorinated organic solvents which are non-ozone depleting to produced highly chlorinated resins. In a preferred embodiment of this invention, the reaction is initiated by chlorinating a $C_{20}$–$C_{24}$ paraffin wax in the molten phase with gaseous chlorine until the level of chlorine in the wax reaches a level of ~50% chlorine. This degree of chlorination is used merely for commercial expedience, and it is contemplated within this invention to achieve chlorination levels at this stage of the reaction, which are both higher and lower than these values. At this point, a light colored liquid material is obtained. Solvent is added in order to reduced viscosity and allow a lower temperature for further chlorination to an ~70% chlorine-containing chlorinated paraffin resin is produced.

However, unlike prior art processes which use $C_1$–$C_2$ chlorinated alkanes as organic solvents, the solvents of this invention are non-ozone depleting halogenated aromatic based with boiling points less than 180° C., amd preferably less than 160° C., and which are non-reactive to chlorine in a free radical environment. In its broadest form, the solvents are halogenated benzenes as shown by formula (I),

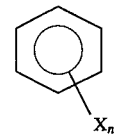

(I)

wherein X is a halogen selected from the group consisting of chlorine, fluorine and bromine and n is an integer from 1 to 6.

Exemplary and non-limiting members of halogenated solvents of formula (I), which are for the purposes of illustration only, would include those solvents such as are shown in Table I.

TABLE I

| Solvent | Flash Point (° C.) | Boiling Point (°C.) |
|---|---|---|
| difluorobenzene (ortho) | 2 | 91–92 |
| difluorobenzene (meta) | 2 | 81 |
| difluorobenzene (para) | 2 | 87 |
| pentafluorobenzene | 10 | 81 |

TABLE I-continued

| Solvent | Flash Point (° C.) | Boiling Point (°C.) |
|---|---|---|
| 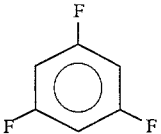 | 10 | 81 |

In addition to the halogenated benzene solvents shown by formula (I), mixed halogenated solvents as shown by formula (II) are envisioned to be a part of this invention,

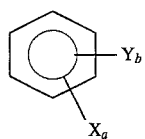 (II)

wherein a is an integer from 1 to 5, b is an integer from 1 to (6-a), and Y is a halogen selected from that defined for X, but not being the same halogen as X.

Exemplary and non-limiting members of halogenated solvents of formula (II), which are for the purposes of illustration only, would include those solvents such as are shown in Table II.

TABLE II

| Solvent | Flash Point (°C.) | Boiling Point (°C.) |
|---|---|---|
| 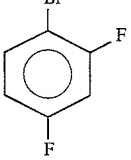 | 51 | 145–146 |
| 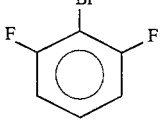 | 53 | 61 (@ 35 mmHg) |
| 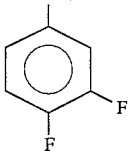 | 33 | 150 |
| 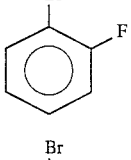 | 43 | 156 |
| 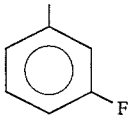 | 38 | 150 |

TABLE II-continued

| Solvent | Flash Point (°C.) | Boiling Point (°C.) |
|---|---|---|
|  | 60 | 151–152 |
| 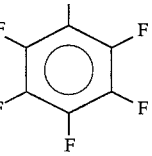 | 87 | 137 |
| 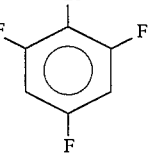 | 110 | 140.5 |
| 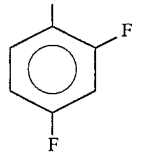 | 32 | 127 |
| 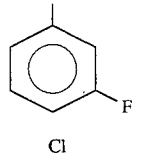 | 20 | 126 |
| 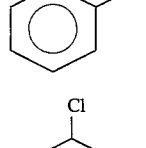 | 31 | 137 |
| 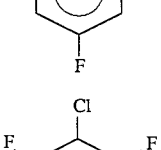 | 29 | 129 |
| 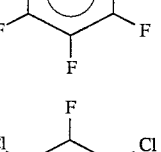 | none | 117 |
| 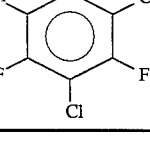 | 102 | melting pt. 62 boiling pt. >160 |

In a preferred embodiment of the invention, the halogenated aromatics are perhalogenated aromatics as shown by formula (III)

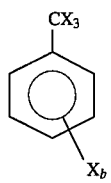  (III)

wherein X is as previously described, and b is an integer from 0 to 5.

Exemplary and non-limiting members of halogenated solvents of formula (III), which are for the purposes of illustration only, would include those solvents such as are shown in Table III.

TABLE III

| Solvent | Flash Point (°C.) | Boiling Point (°C.) |
|---|---|---|
| CF₃-C₆H₅ | 12 | 101–102 |

In a more preferred embodiment of the invention, the halogenated aromatic will be a perhalogenated aromatic as shown by formula (IV)

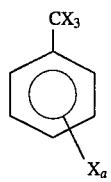  (IV)

wherein a is an integer from 1 to 5.

Exemplary and non-limiting members of halogenated solvents of formula (IV), which are for the purposes of illustration only, would include those solvents such as are shown in Table IV.

TABLE III

| Solvent | Flash Point (°C.) | Boiling Point (°C.) |
|---|---|---|
| CF₃-C₆F₅ | 20 | 103 |

In a most preferred embodiment of the invention, the halogenated aromatics contain at least one perhalogenated substituent and at least one other halogenated substituent as shown by formula (V)

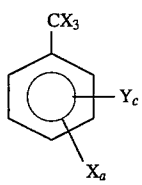  (V)

wherein X and a are as defined previously, Y is a halogen selected from that defined for X, but not being the same as X, and c is an integer from 0 to (4-a).

Exemplary and non-limiting members of halogenated solvents of formula (V), which are for the purposes of illustration only, would include those solvents such as are shown in Table V.

TABLE V

| Solvent | Flash Point (°C.) | Boiling Point (°C.) |
|---|---|---|
| 4-Cl-C₆H₄-CF₃ | 43 | 139 |
| 2-Cl-C₆H₄-CF₃ | 51 | 159 |
| 1:1 blend of 4-Cl-C₆H₄-CF₃ and 2-Cl-C₆H₄-CF₃ | 48 | 142–159 |
| 2-Br-C₆H₄-CF₃ | 51 | 167–168 |
| 3-Br-C₆H₄-CF₃ | 43 | 153–154 |
| 4-Br-C₆H₄-CF₃ | 48 | 154 |
| 3-Cl-C₆H₄-CF₃ | 36 | 137–138 |

TABLE V-continued

| Solvent | Flash Point (°C.) | Boiling Point (°C.) |
| --- | --- | --- |
| 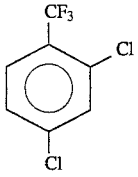 | 72 | 177–178 |
| 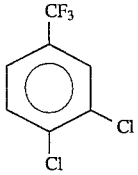 | 65 | 173 |

While for certain applications, an unstabilized chlorinated resin may be acceptable. It is envisioned that stabilizers will be added to the eventual product.

EXAMPLES

The best mode for carrying out the invention will now be described for the purposes of illustrating the best mode known to the applicant at the time. The examples are illustrative only and not meant to limit the invention, as measured by the scope and spirit of the claims.

Example #1-Conventional Preparation of Chlorinated Resin

A 1 L, 4-necked flask, equipped with a mechanical stirrer, pot thermometer, reflux condenser and gas addition tube was charged with 130 g molten Shellwax® 100, a normal paraffin wax in the $C_{20-24}$ range, and 450 g $CCl_4$ solvent. The mixture was warmed to about 45° C. to give a homogeneous solution. Chlorine gas was added with warming until reflux temperature, ~77° C. was reached. The initial solution was a yellow-green color due at least in part, to the saturated chlorine. As the chlorination process neared reflux, the solution turned virtually colorless and many small bubbles of HCl gas began to effervesce from the solution. At this point, UV or fluorescent light was used to accelerate the reaction.

The reaction was allowed to continue for between 8–10 hours at reflux, at which point the solution typically turns hazy in color. Shortly before the haze develops, the reaction had proceeded to a 70–71% level of chlorination in the resin backbone. The chlorine flow was stopped and nitrogen or air passed through to expel HCl and $Cl_2$ from the solution. When the acid content is low enough, stabilizers such as epoxidized soy bean oil are added at the desired level, typically 0.1 to 1.0% of the chlorinated resin. The solution was stripped of solvent by distillation and the molten chlorinated wax poured out onto a cool surface where it solidified into a brittle glassy solid. If desired, the chlorinated solid resin is mechanically broken as desired. Physical properties of the chlorinated resin produced in Example #1 are shown in Table VI:

TABLE VI

| Parameter | Measurement |
| --- | --- |
| Chlorine Content (%) | 70.6 |
| Solution color (10 g in 90 g $CCl_4$, APHA) | 50 |
| Softening Point (°C.) Ring and Ball Method | 108 |
| Thermal Stability (% HCl liberated at 175° C. for 4 hours) | 0.05 |
| % Residual Solvent | 0.06 |

Example #2-Chlorinated Resin Synthesis using Non-Ozone Depleting Solvent

A one-liter 4-necked flask equipped with a mechanical stirrer, pot thermometer, reflux condenser and gas addition tube was charged with 166 g of Shellwax® 100, (Shell Chemical Co.) chlorinated to a level of ~35.9% chlorine. Then 299.8 g of Oxol® 100, tradename for 4-chlorobenzotrifluoride solvent, is charged to the partially chlorinated Shellwax® 100. The mixture was warmed to ~50° C. to give a homogeneous solution. Chlorine gas was added with warming until a temperature of about 77° C. was reached. At this point, chlorine was introduced and a fluorescent light was used to catalyze the reaction. The reaction was allowed to continue for 9 hours at 75°–80° C. After 9 hours, the chlorine flow was stopped and nitrogen gas was passed through to expel HCl and chlorine from the solution. When the acid content is low enough, stabilizer such as epoxidized soybean oil is added at the desired level, typically 0.1 to 1% of the chlorinated resin. The solution was stripped of solvent by distillation and the molten chlorinated wax was poured onto a cool surface where it solidified into a brittle glassy solid. If desired, the chlorinated solid may be mechanically broken up. The properties of the chlorinated resin produced in Example #2 are shown in Table VII.

TABLE VII

| Parameter | Measurement |
| --- | --- |
| Chlorine Content (%) | 71.0 |
| Solution color (10 g in 90 g $CCl_4$, APHA) | 40 |
| Softening Point (°C.) Ring and Ball Method | 110 |
| Thermal Stability (% HCl liberated at 175° C. for 4 hours) | 0.05 |
| % Residual Solvent | 0.09 |

As is seen from a comparison of the data contained in Tables I and II, a chlorinated resin with excellent properties can be produced from a non-ozone depleting solvent. The physical properties of Example #2 are equivalent to the properties of Example #1 which uses an ozone-depleting solvent.

DISCUSSION

In an ever increasing regulatory environment, and with depletion of the ozone layer apparently occurring at increasing rates, the need for a non-ozone depleting solvent is becoming critical. In addition to non-ozone depleting characteristics, the solvent should have a flash point which is as high as possible, in a preferred embodiment, this being at least 40° C., and a boiling point of no more than ~160° C.

In using the non-ozone depleting solvent procedure of this invention, it is recognized that the chlorination of the paraffin wax can occur with praffin wax which has previously been chlorinated, although this is not a precondition to the use of the solvents of the invention.

Thus what is taught is that non-ozone depleting solvents of generic formula (VI)

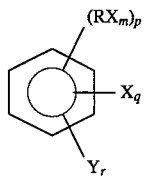
(VI)

wherein R is an alkyl radical from 1 to 6 carbons, X and Y are different halogens selected from the group consisting of fluorine, bromine and chlorine, m is an integer necessary to satisfy the covalent bonds to R, and p, q, and r are integers from 0 to 6, with the limitation that p+q+r must be less than or equal to 6, and also greater than or equal to 1.

The invention has been described with reference to preferred and alternate embodiments. Obviously, modifications and alterations will occur to others upon the reading and understanding of the specification. It is intended to include all such modifications and alterations insofar as they come within the scope of the appended claims or the equivalents thereof.

What is claimed is:

1. In a process for the chlorination of a paraffin wax, wherein the wax is heated to a temperature sufficient to produce a molten wax in a solvent, the wax being chlorinated with a chlorinating agent at a temperature sufficient to produce a chlorinated molten wax; the improvement comprising the use of a non-ozone depleting aromatic solvent or blends thereof, with a boiling point less than 160° C. and which is non-reactive to chlorine in a free radical chlorination environment wherein the solvent is a halogenated benzene as shown by formula (I)

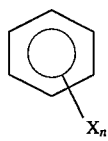
(I)

wherein X is a halogen selected from the group consisting of chlorine, fluorine and bromine and n is an integer from 1 to 6.

2. The process of claim 1 wherein the solvent is a mixed halogenated solvent as shown by formula (II),

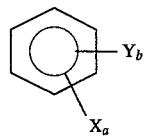
(II)

wherein a is an integer from 1 to 5. b is an integer from 1 to (6-a), and Y is a halogen selected from that defined for X, but not being the same as X.

3. The process of claim 1 which further comprises the step of adding a stabilizer.

4. In a process for the chlorination of a paraffin wax, wherein the wax is heated to a temperature sufficient to produce a molten wax in a solvent, the wax being chlorinated with a chlorinating agent at a temperature sufficient to produce a chlorinated molten wax; the improvement comprising the use of a non-ozone depleting aromatic solvent of formula (VI)

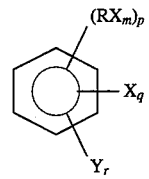
(VI)

wherein R is an alkyl radical from 1 to 6 carbons, X and Y are different halogens selected from the group consisting of fluorine, bromine and chlorine, m is an integer necessary to satisfy the covalent bonds to R, and p, q, and r are integers from 0 to 6, with the limitation that p+q+r must be less than or equal to 6, and also greater than or equal to 1, or blends thereof, and which is non-reactive to chlorine in a free radical chlorination environment.

5. The process of claim 4 wherein the solvent is a halogenated benzene as shown by formula (I),

(I)

wherein n is an integer from 1 to 6.

6. The process of claim 5 wherein the solvent is a mixed halogenated solvent as shown by formula (II),

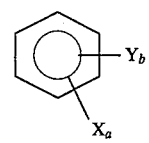
(II)

wherein a is an integer from 1 to 5, b is an integer from 1 to (6-a), and Y is a halogen selected from that defined for X, but not being the same as X.

7. The process of claim 4 wherein the solvent is a perhalogenated aromatic as shown by formula (III)

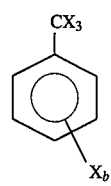
(III)

wherein b is an integer from 0 to 5.

8. The process of claim 7 wherein the solvent is a perhalogenated aromatic as shown by formula (IV)

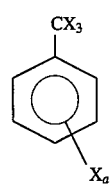
(IV)

and wherein a is an integer from 1 to 5.

9. The process of claim 8 wherein the solvent is a perhalogenated aromatic as shown by formula (V)

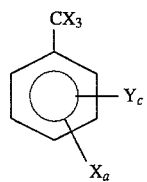
(V)
wherein Y is a halogen selected from that defined for X, but not being the same as X and c is an integer from 0 to (4-a).
10. The process of claim 8 wherein the solvent is selected from the group consisting of:
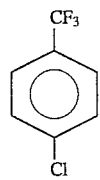
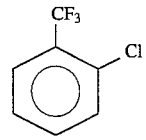
and
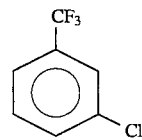
and mixtures thereof.
11. The process of claim 4 which further comprises the step of adding a stabilizer.
* * * * *